(12) United States Patent
Mizuno et al.

(10) Patent No.: US 10,488,316 B2
(45) Date of Patent: Nov. 26, 2019

(54) FINE-PARTICLE NUMBER MEASUREMENT DEVICE AND FINE-PARTICLE NUMBER MEASUREMENT METHOD

(71) Applicant: NGK INSULATORS, LTD., Nagoya (JP)

(72) Inventors: Kazuyuki Mizuno, Nagoya (JP); Kenshin Kitoh, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 383 days.

(21) Appl. No.: 15/271,590

(22) Filed: Sep. 21, 2016

(65) Prior Publication Data

US 2017/0010202 A1 Jan. 12, 2017

Related U.S. Application Data

(63) Continuation of application No. PCT/JP2015/055583, filed on Feb. 26, 2015.

(30) Foreign Application Priority Data

Mar. 26, 2014 (JP) .................................. 2014-062854
May 13, 2014 (JP) .................................. 2014-099176

(51) Int. Cl.
*G01N 15/06* (2006.01)
*B03C 3/017* (2006.01)
(Continued)

(52) U.S. Cl.
CPC ......... *G01N 15/0656* (2013.01); *B03C 3/017* (2013.01); *B03C 3/41* (2013.01);
(Continued)

(58) Field of Classification Search
CPC ... G01N 2015/1062; G01N 2015/1486; G01R 31/12; G02B 5/3008
See application file for complete search history.

(56) References Cited

U.S. PATENT DOCUMENTS 7,518,108 B2 * 4/2009 Frey .................... H01J 49/0045
250/281
2009/0308251 A1 12/2009 Kondou et al.
(Continued)

FOREIGN PATENT DOCUMENTS

EP 2 860 510 A1 4/2015
JP 2012-026892 A1 2/2012
(Continued)

OTHER PUBLICATIONS

Japanese Office Action (Application No. 2016-510156) dated Jan. 30, 2018 (with English translation).
(Continued)

*Primary Examiner* — Tung X Nguyen
(74) *Attorney, Agent, or Firm* — Burr & Brown, PLLC (57) ABSTRACT

In a particle counter and a method of counting a number of particles, the particle counter includes a casing made of a ceramic, an electric charge adder configured to add electric charges to particles in a measurement target gas supplied into the casing, a first electric charge collector configured to collect the electric charges added to the particles, and a number measuring unit configured to measure a number of the particles based on a quantity of the collected electric charges.

9 Claims, 4 Drawing Sheets

(51) Int. Cl.
  *B03C 3/41* (2006.01)
  *B03C 3/47* (2006.01)
  *G01N 15/00* (2006.01)

(52) U.S. Cl.
  CPC .......... *B03C 3/47* (2013.01); *B03C 2201/06* (2013.01); *F01N 2560/05* (2013.01); *G01N 2015/0046* (2013.01)

(56) References Cited

U.S. PATENT DOCUMENTS

| | | |
|---|---|---|
| 2010/0192670 A1 | 8/2010 | Schaenzlin et al. |
| 2012/0017666 A1 | 1/2012 | Otsuki et al. |
| 2012/0234172 A1 | 9/2012 | Sugiyama et al. |
| 2015/0020574 A1* | 1/2015 | Motomura ......... G01N 15/0656 73/23.31 |

FOREIGN PATENT DOCUMENTS

| | | |
|---|---|---|
| JP | 2012-194078 A1 | 10/2012 |
| WO | 2008/111403 A1 | 9/2008 |
| WO | 2013/125181 A1 | 8/2013 |
| WO | 20130125181 † | 8/2013 |
| WO | WO 2013/183652 A1 | 12/2013 |

OTHER PUBLICATIONS

International Search Report and Written Opinion (Application No. PCT/JP2015/055583) dated May 26, 2015.
Extended European Search Report (Application No. 15768899.5) dated Oct. 19, 2017.
Observations by Third Parties, European Application No. 15768899.5, dated Jun. 22, 2017 (10 pages).

\* cited by examiner
† cited by third party

FINE-PARTICLE NUMBER MEASUREMENT DEVICE AND FINE-PARTICLE NUMBER MEASUREMENT METHOD

CROSS-REFERENCE TO RELATED APPLICATIONS

This application is a Continuation of International Application No. PCT/JP2015/055583 filed on Feb. 26, 2015, which is based upon and claims the benefit of priority from Japanese Patent Applications No. 2014-062854 filed on Mar. 26, 2014 and No. 2014-099176 filed on May 13, 2014, the contents all of which are incorporated herein by reference.

TECHNICAL FIELD

The present invention relates to a particle counter for counting the number of particles (fine-particle number measurement device) in a gas. Further, the present invention relates to a method of counting the number of particles (fine-particle number measurement method).

BACKGROUND ART

In general, as a measurement instrument or as a measurement method for measurement of particles, it has been known to use a particle mass counter for counting the particle mass of particles.

An FCAE (Faraday Cup Aerosol Electrometer) and a PM sensor, as described in Japanese Laid-Open Patent Publication No. 2012-194078, are examples of such a particle mass counter.

A CPC (Condensation Particle Counter), as described in Japanese Laid-Open Patent Publication No. 2012-026892, is an example of a particle counter for counting the number of particles. In such a CPC, organic gases of alcohol, butanol, etc., are mixed in a saturated state and adhered to particles in the exhaust gas. The particles grow to have an increased particle size. Following growth of the particles, the particles are discharged through slits. Then, laser light is irradiated onto the discharged particles in order to count the number of particles.

SUMMARY OF INVENTION

However, conventional approaches for counting the number of particles use a PMP (Particle Measurement Program) system, which is based on the premise of carrying out the measurement method in a stationary application. For example, in the case of measuring particles in an exhaust gas emitted from a vehicle, the size of the PMP system is larger than the vehicle. Further, the measurement instrument itself has a stack size determined by stacking several casings, each having a longitudinal size in a range of about 30 to 50 cm, a lateral size in a range of about 30 to 50 cm, and a vertical size in a range of about 10 to 15 cm. The measurement instrument is not intended to be used in vehicles or ordinary homes. Further, in the case of counting the number of particles using a CPC, since organic gases of alcohol, butanol, etc., are used, there may be some problems or difficulties in relation to management of such gases.

As a method of counting the number of particles, in one possible method, for example, based on the idea that a certain correlation is present between the mass and the number of particles, the mass of certain specified particles is converted into the number of particles. However, it takes time for obtaining a correlation between the mass and the number of particles. Further, it is considered that the correlation, etc., may change depending on the environment of use. Therefore, there may be some problems in relation to calibration, etc.

The present invention has been made taking into consideration problems of this type, and an object of the present invention is to provide a particle counter for counting the number of particles as well as a method of counting the number of particles, in which it is possible to reduce the size and weight of the particle counter. In addition, the particle counter and the method can be used suitably in vehicles or in ordinary homes, and the number of particles can be counted accurately.

[1] A particle counter according to a first aspect of the invention includes a casing made of ceramic, an electric charge adder configured to add electric charges to particles in a measurement target gas supplied into the casing, an electric charge collector configured to collect the electric charges added to the particles, and a number measuring unit configured to measure a number of the particles based on a quantity of the collected electric charges.

[2] In the first aspect of the invention, the particle counter may include a heater configured to heat a portion where the electric charges are collected.

[3] In the first aspect of the invention, the particle counter may include a switch configured to electrically connect the electric charge collector and the number measuring unit at fixed time intervals, and the number measuring unit may measure an electric current based on the quantity of the collected electric charges.

[4] In this case, a serial circuit including a capacitor and a resistor may be connected to the electric charge collector, and when the electric charge collector and the number measuring unit are electrically connected by the switch, generation of electric current based on the electric charges collected by the electric charge collector may be signaled to the number measuring unit as a transient response through the serial circuit.

[5] In the first aspect of the invention, the electric charge collector may include a measurement electrode provided in the casing, and at least one electric field generator configured to generate an electric field in the casing. In addition, the electric charges added to the particles may be collected at the measurement electrode by the electric field.

[6] In this case, the electric field generator of the electric charge collector may include a negative electrode provided in the casing at a position deeper than an inlet of the particles, and a positive electrode provided in opposition to the negative electrode. In addition, the measurement electrode of the electric charge collector may be provided between the negative electrode and the positive electrode, and may be arranged in vicinity of the positive electrode.

[7] In the first aspect of the invention, the electric charge adder may include a needle electrode oriented toward an inlet of the particles in the casing, and a counter electrode provided in opposition to a front end of the needle electrode. In addition, corona discharge is generated between the needle electrode and the counter electrode by a potential difference between the needle electrode and the counter electrode.

[8] In the first aspect of the invention, the particle counter may include at least one electric field generator, together with a second electric charge collector configured to collect electric charges that have not been added to the particles.

[9] A particle counter according to a second aspect of the invention includes a casing made of ceramic, an electric charge adder configured to add electric charges to particles in a measurement target gas supplied into the casing, an electric charge collector configured to collect only electric charges that have not been added to the particles, and a number measuring unit configured to measure a number of the particles based on a quantity of the collected electric charges.

[10] In the second aspect of the invention, the particle counter may include a heater configured to heat a portion where the electric charges are collected.

[11] In the second aspect of the invention, the particle counter may include a switch electrically connecting the electric charge collector and the number measuring unit, and the number measuring unit may measure an electric current based on the quantity of the collected electric charges.

[12] In this case, a serial circuit including a capacitor and a resistor may be connected to the electric charge collector, and when the electric charge collector and the number measuring unit are electrically connected by the switch, generation of electric current based on the electric charges collected by the electric charge collector may be signaled to the number measuring unit as a transient response through the serial circuit.

[13] In the second aspect of the invention, the electric charge collector may include a measurement electrode provided in the casing, and at least one electric field generator configured to generate an electric field in the casing, and only the electric charges that have not been added to the particles may be collected at the measurement electrode by the electric field.

[14] In this case, the electric field generator of the electric charge collector may include a negative electrode provided in the casing at a position deeper than an inlet of the particles, and a positive electrode provided in opposition to the negative electrode. In addition, the measurement electrode of the electric charge collector may be provided between the negative electrode and the positive electrode, and may be arranged in vicinity of the positive electrode.

[15] In the second aspect of the invention, the electric charge adder may include a needle electrode oriented toward an inlet of the particles in the casing, and a counter electrode provided in opposition to a front end of the needle electrode. In addition, corona discharge may be generated between the needle electrode and the counter electrode by a potential difference between the needle electrode and the counter electrode.

[16] In the second aspect of the invention, the particle counter may include a member configured to remove particles larger than a predetermined size, which is disposed at a portion where the particles are supplied.

[17] A method of counting a number of particles according to a third aspect of the invention includes the steps of adding electric charges to particles in a measurement target gas supplied into a casing made of ceramic, collecting the electric charges added to the particles, and measuring the number of the particles based on a quantity of the collected electric charges.

[18] A method of counting a number of particles according to a fourth aspect of the invention includes the steps of adding electric charges to particles in a measurement target gas supplied into a casing made of ceramic, collecting only electric charges that have not been added to the particles, and measuring the number of the particles based on a quantity of the collected electric charges.

In accordance with the particle counter and the method of counting the number of particles according to the present invention, it is possible to reduce the size and weight of the particle counter, while in addition, the particle counter and the method can be used suitably in vehicles or in ordinary homes, and the number of particles can be counted accurately.

DESCRIPTION OF EMBODIMENTS

Hereinafter, exemplary embodiments of a particle counter and a method of counting the number of particles according to the present invention will be described with reference to FIGS. 1 to 4. It should be noted that, in the present description, a numeric range of "A to B" includes both the numeric values A and B as lower and upper limit values.

Figure 1:
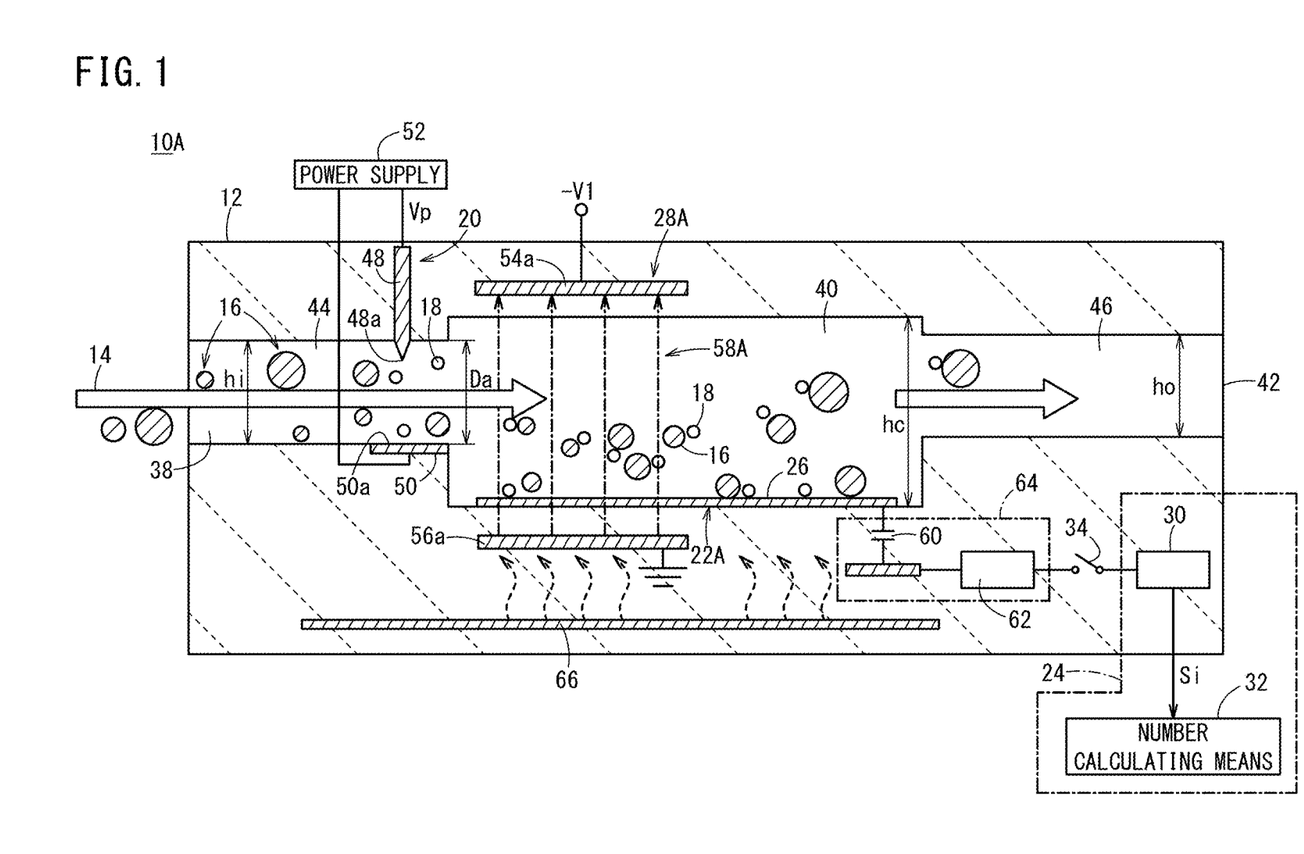
FIG. 1 is a diagram showing the structure of a particle counter according to a first embodiment of the present invention.

At first, a particle counter according to a first embodiment (hereinafter referred to as a "first particle counter 10A") will be described. As shown in FIG. 1, the first particle counter 10A includes a casing 12 made of ceramic, an electric charge adding means (electric charge adder) 20 for adding electric charges 18 to particles 16 in a measurement target gas 14 supplied into the casing 12, a first electric charge collecting means (electric charge collector) 22A for collecting the electric charges 18 added to the particles 16, and a number measuring means (number measuring unit) 24 for measuring the number of the particles based on the quantity of the collected electric charges 18.

The first electric charge collecting means 22A includes a measurement electrode 26 provided in the casing 12, and a first electric field generating means (electric field generator) 28A for generating an electric field in the casing 12. After the electric charges 18 have been added to the particles 16, in the presence of the electric field, the particles 16 are adhered to the measurement electrode 26. That is, the electric charges 18 that are added to the particles 16 are collected at the measurement electrode 26.

The number measuring means 24 includes an electric current measuring unit 30 and a number calculating means 32 for calculating the number of the particles 16 adhered to the measurement electrode 26 over a predetermined time period (e.g., 1 to 5 minutes) based on a detection signal Si (detected electric current value) from the electric current measuring unit 30.

Further, the first particle counter 10A includes a switch 34 for electrically connecting the measurement electrode 26 of the first electric charge collecting means 22A and the current measuring unit 30 of the number measuring means 24 at intervals of a fixed time period (e.g., 5 to 15 seconds).

The casing 12 includes a gas supply port 38 for allowing the measurement target gas 14 to be supplied into the casing 12 through the gas supply port 38, a hollow portion 40 for diffusing the particles 16 supplied into the casing 12, and a gas discharge port 42 for discharging the particles 16 to the outside of the casing 12.

A gas inlet 44 having a certain height hi is provided between the gas supply port 38 and the hollow portion 40, and a gas outlet 46 having a certain height ho is provided between the hollow portion 40 and the gas discharge port 42. The height hi of the gas inlet 44 and the height hc of the hollow portion 40 satisfy the relationship hc≥hi. For example, the height hi of the gas inlet 44 and the height ho of the gas outlet 46 may be in the range of 200 µm to several cm, and the height hc of the hollow portion 40 is in the range of 200 µm to several cm. The height hi of the gas inlet 44 and the height ho of the gas outlet 46 may be the same, or they may be different.

The casing 12 is made of a ceramic material. For example, a ceramic material having insulating properties and high heat resistance such as alumina, mullite, or silicon nitride may be used.

The electric charge adding means 20 is oriented toward the gas inlet 44 of the casing 12, and includes a needle electrode 48 in a needle shape having an acute front end 48a, a counter electrode 50 provided in opposition to the front end 48a of the needle electrode 48, and a power supply 52 for applying a voltage Vp (e.g., a pulse voltage) between the needle electrode 48 and the counter electrode 50. The distance Da between the front end 48a of the needle electrode 48 and a counter surface 50a (a surface provided in opposition to the needle electrode 48) of the counter electrode 50 lies within a range of 200 µm to several cm. Further, when the voltage Vp is applied between the needle electrode 48 and the counter electrode 50, a corona discharge is generated between the needle electrode 48 and the counter electrode 50 by the potential difference between the needle electrode 48 and the counter electrode 50. The measurement target gas 14 passes through the corona discharge so as to add one piece of electric charge 18 (an electron in this example) to each of the particles 16 in the measurement target gas 14. After the one piece of electric charge 18 has been added to each of the particles 16, the particles 16 move into the hollow portion 40.

The reason why one piece of electric charge 18 is added to each of the particles 16 is described in G. Biskos, E. Mastorakos, N. Collings "Monte-Carlo simulation of uni-polar diffusion charging for spherical and non-spherical particles". As for the electric charge, by adjusting the design values therefor, two or more pieces of electric charge may be added to each of the particles 16. The design values as referred to herein are ion concentration and time.

For example, when electrons collide with particles 16 such as soot, the particles 16 are charged electrically with the electrons. Since a repulsive force is generated between the electrically charged particles 16 and the electrons, further charging of the particles 16 does not occur easily, i.e., two or more electrons are not easily added to each of the particles 16. The electrons are preferentially added to particles 16 that have not been charged electrically. As a result, the number of particles 16 having one electron is increased.

If the distance Da between the needle electrode 48 and the counter electrode 50 is 2 cm, a voltage Vp of about 2.5 kV is needed in order to generate a corona discharge between the needle electrode 48 and the counter electrode 50.

The first electric field generating means 28A of the first electric charge collecting means 22A includes a first negative electrode 54a provided in the hollow portion 40 of the casing 12, and a first positive electrode 56a disposed in opposition to the first negative electrode 54a. The measurement electrode 26 of the first electric charge collecting means 22A is provided between the first negative electrode 54a and the first positive electrode 56a, and is disposed in the vicinity of the first positive electrode 56a. A negative potential −V1 is applied to the first negative electrode 54a, and a ground potential Vss is applied to the first positive electrode 56a. The level of the negative potential −V1 is on the order of −mV to several tens V. By such a negative potential −V1, a first electric field 58A is generated, which is oriented from the first positive electrode 56a toward the first negative electrode 54a. Therefore, the particles 16 (having the electric charges 18) that have entered into the hollow portion 40 are drawn toward the first positive electrode 56a by the generated first electric field 58A, and the particles 16 become adhered to the measurement electrode 26 provided in an intermediate position on the way to the first positive electrode 56a.

In this regard, if the flow rate of the measurement target gas 14 supplied into the gas inlet 44 is to be determined beforehand, it is preferable to determine the layout positions of the first negative electrode 54a and the first positive electrode 56a of the first electric field generating means 28A, as well as the magnitude of the potential applied to the first negative electrode 54a, so as to satisfy the following conditions (a) and (b).

(a) Large particles 16 having a particle size (mass median diameter or count median diameter) of 2.5 µm or more are directly discharged to the outside through the gas outlet 46 and the gas discharge port 42.

(b) Small particles 16 having a particle size (mass median diameter or count median diameter) of less than 2.5 µm are adhered to the measurement electrode 26.

Further, in the first particle counter 10A, a serial circuit 64 including a capacitor 60 and a resistor 62 is connected to the measurement electrode 26, and the above-described switch 34 is connected between the serial circuit 64 and the current measuring unit 30. As the switch 34, preferably, for example, a semiconductor switch may be used.

Therefore, when an on-operation of the switch 34 is performed, and the measurement electrode 26 and the current measuring unit 30 are connected electrically, an electric current I based on the electric charges 18 that were added to the particles 16 adhered to the measurement electrode 26 is signaled to the current measuring unit 30 as a transient response through the serial circuit 64. As the current measuring unit 30, a common ammeter may be used. For example, a system for measuring an electric current value from the voltage applied to both terminals of an internal resistance connected in series with the serial circuit 64, and a system using a shunt may be adopted.

The relationship between the current I and the electric charge quantity q is as shown by the following equations.

$$I = dq/(dt)$$

$$q = \int I \, dt$$

Therefore, in order to determine an integrated value (accumulated electric charge quantity) of the electric current values, the number calculating means 32 integrates (accumulates) the electric current values from the current measuring unit 30 over a period of time in which the on-operation of the switch 34 is performed (ON period). The number of particles 16 that become adhered to the measurement electrode 26 over a fixed time period (e.g., 5 to 15 seconds) can be determined after the elapse of the ON period by dividing the accumulated electric charge quantity by the electric charge quantity of one piece of electric charge.

Further, the number calculating means 32 repeats the computation of calculating the number of the particles 16 in the fixed time period over a predetermined time period (e.g., 1 to 5 minutes), and integrates the obtained values in order to calculate the number of particles 16 that become adhered to the measurement electrode 26 over the predetermined time period.

By utilizing the transient response in accordance with the capacitor 60 and the resistor 62, it becomes possible to measure even small electric currents, and to detect the number of particles 16 with a high degree of accuracy. By adopting a resistor having a large resistance value, a minute current in the order of pA (pico amperes) or nA (nano amperes) can be measured, for example, using a large time constant.

Further, the first particle counter 10A includes a heater 66 for heating a portion (e.g., the measurement electrode 26) where the electric charges are collected. The advantages of using such a heater 66 will be described below.

(a) Measurement is performed in a state in which the influence of a polymer hydrocarbon referred to as SOF (Soluble Organic Fraction) is removed. In such a measurement, an improvement in accuracy is achieved.

(b) Particles (e.g., soot) accumulated in the casing are burned periodically for the purpose of refreshment.

As described above, although particles 16 having a particle size of 2.5 μm or more are discharged to the outside, since particles 16 having a particle size of less than 2.5 μm and which have entered into the hollow portion 40 are made to move toward the measurement electrode 26 by the first electric field 58A, the particles 16 become adhered to the measurement electrode 26 without being discharged to the outside. Therefore, by periodically heating the measurement electrode 26 using the heater 66, the particles 16 that are adhered to the measurement electrode 26 can easily be removed.

As described above, the first particle counter 10A utilizes a small space in which the height hi of the gas inlet 44 and the height ho of the gas outlet 46 lie within a range of 200 μm to several cm, and the height hc of the hollow portion 40 lies within a range of 200 μm to several cm. The electric charges 18 are added to the particles 16 in the measurement target gas 14 that is supplied into the casing 12. Further, the particles 16 that have entered the hollow portion 40 become adhered to the measurement electrode 26 due to the first electric field 58A. In such a configuration, by using the switch 34 to electrically connect the measurement electrode 26 and the current measuring unit 30, it is possible to easily detect the number of particles 16 that are adhered to the measurement electrode 26. Further, a reduction in size and weight can be facilitated. Therefore, the first particle counter 10A can suitably be used in vehicles and ordinary homes (for example, the first particle counter 10A can be attached to a gas exhaust portion of an air conditioner or the like).

Figure 2:
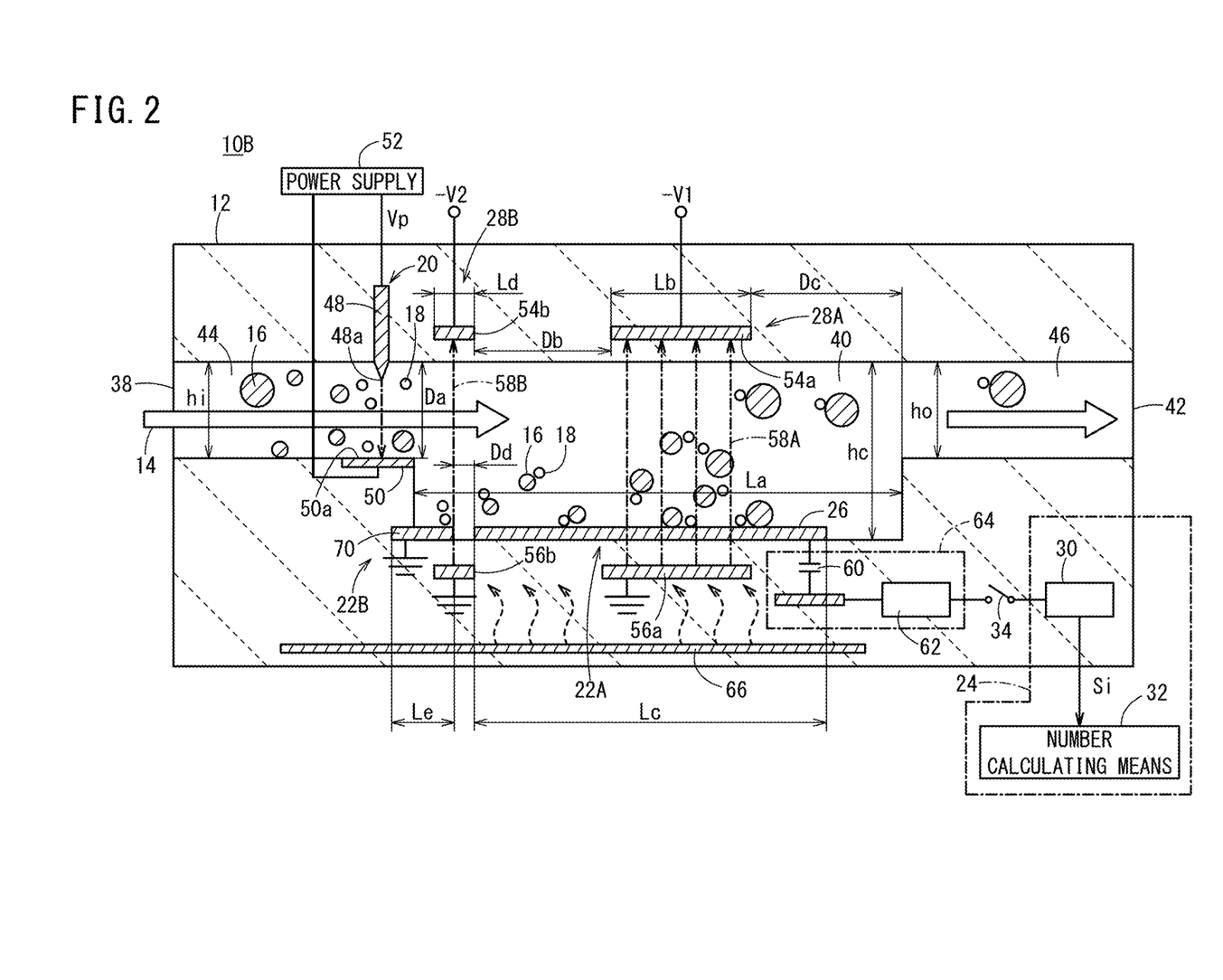
FIG. 2 is a diagram showing the structure of a particle counter according to a second embodiment of the present invention.

Next, a particle counter according to a second embodiment (hereinafter referred to as a second particle counter 10B) will be described with reference to FIG. 2.

The second particle counter 10B has substantially the same structure as the first particle counter 10A. However, the second particle counter 10B differs from the first particle counter 10A in that the second particle counter 10B includes a second electric charge collecting means (second electric charge collector) 22B for collecting electric charges 18 that have not been added to the particles 16. The second electric charge collecting means 22B includes a second electric field generating means (electric field generator) 28B and a collecting electrode 70.

The second electric field generating means 28B includes in the hollow portion 40 a second negative electrode 54b, which is positioned in the vicinity of the gas inlet 44, and a second positive electrode 56b disposed in opposition to the second negative electrode 54b. The collecting electrode 70 is provided between the second negative electrode 54b and the second positive electrode 56b, and is disposed in the vicinity of the second positive electrode 56b. A second negative potential −V2 is applied to the second negative electrode 54b, and a ground potential Vss is applied to the second positive electrode 56b. The absolute value of the second negative potential −V2 is smaller by one or more orders of magnitude than the absolute value of the first negative potential −V1 that is applied to the first negative electrode 54a of the first electric field generating means 28A in the first electric charge collecting means 22A.

Therefore, a weak second electric field 58B is generated, which is oriented from the second positive electrode 56b toward the second negative electrode 54b. Thus, among the electric charges 18 generated by corona discharge in the electric charge adding means 20, electric charges 18 that have not been added to the particles 16 are drawn toward the second positive electrode 56b by the generated weak second electric field 58B, and the electric charges 18 are discharged to GND through the collecting electrode 70, which is disposed at an intermediate position on the way to the second positive electrode 56b.

Next, relative lengths of the hollow portion 40 and various electrodes, i.e., relative lengths thereof in the direction from the gas supply port 38 to the gas discharge port 42, will be described.

First, assuming that the length La of the hollow portion 40 is 100, and the lengths Lb of the first negative electrode 54a and the first positive electrode 56a lie within a range of 28 to 34, the length Lc of the measurement electrode 26 lies within a range of 74 to 78, the length Ld of the second negative electrode 54b and the second positive electrode 56b lies within a range of 5 to 10, and the length Le of the collecting electrode 70 lies within a range of 5 to 10. Further, the spacing distance Db between the second negative electrode 54b and the first negative electrode 54a lies within a range of 28 to 34, the distance Dc from an end of the first negative electrode 54a on the gas discharge port side to the gas discharge port 42 lies within a range of 28 to 34, and the spacing distance Dd between the collecting electrode 70 and the measurement electrode 26 lies within a range of 2 to 5.

By configuring the relative distances in this manner, any unnecessary electric charges 18 that have not been added to the particles 16 mostly do not reach the measurement electrode 26. Further, particles 16 that do not have electric charges 18 do not become adhered to the collecting electrode 70.

In the second particle counter 10B as well, the same working effects and advantages as those of the above-described first particle counter 10A are obtained. In particular, in the second particle counter 10B, any unnecessary electric charges 18 that have not been added to the particles 16 mostly do not reach the measurement electrode 26, and such unnecessary electric charges are discarded to GND through the collecting electrode 70. Therefore, detection errors due to such unnecessary electric charges 18 can be reduced, and an improvement in detection accuracy can be achieved. Further, since the length of the measurement electrode 26 is twice or more as large as the lengths of the first negative electrode 54a and the first positive electrode 56a, particles 16 having various particle sizes of less than 2.5 µm can become adhered to the measurement electrode 26.

In the above example, one first electric field generating means 28A is provided in the first electric charge collecting means 22A. However, alternatively, a plurality of first electric field generating means 28A may be provided.

Next, a particle counter according to a third embodiment (hereinafter referred to as a third particle counter 10C) will be described with reference to FIGS. 3 and 4.

The third particle counter 10C indirectly measures the number of particles 16 by measuring the number of electric charges 18 that have not been added to the particles 16.

More specifically, the third particle counter 10C has the same structure as that of the above-described first particle counter 10A. However, as shown in FIGS. 3 and 4, the third particle counter 10C differs from the first particle counter 10A in that a third electric charge collecting means (electric charge collector) 22C is provided instead of the first electric charge collecting means 22A.

The third electric charge collecting means 22C includes a measurement electrode 26 provided in the casing 12, and a third electric field generating means (electric field generator) 28C for generating an electric field in the casing 12. Electric charges 18 that have not been added to the particles 16 become adhered to the measurement electrode 26 due to the electric field. That is, the electric charges 18 that have not been added to the particles 16 are collected at the measurement electrode 26.

The third electric field generating means 28C includes a third negative electrode 54c, which is positioned in the vicinity of the gas outlet 46 within the hollow portion 40, and a third positive electrode 56c disposed in opposition to the third negative electrode 54c. The measurement electrode 26 is provided between the third negative electrode 54c and the third positive electrode 56c, and is arranged in the vicinity of the third positive electrode 56c. In particular, within the hollow portion 40, the measurement electrode 26 is formed over an area from a position in the vicinity of the gas inlet 44 to a position in the vicinity of the gas outlet 46.

A third negative potential $-V3$ is applied to the third negative electrode 54c, and a ground potential Vss is applied to the third positive electrode 56c. The absolute value of the third negative potential $-V3$ lies within a range of about $\frac{1}{5}$ to $\frac{1}{20}$ of the absolute value of the first negative potential $-V1$ that is applied to the first negative electrode 54a of the first electric charge collecting means 22A.

The height hc of the hollow portion 40 and the height ho of the gas outlet 46 may satisfy the relationship hc ho, or may satisfy the relationship hc ≤ ho. Preferably, the height hc and the height ho are substantially the same. The expression "substantially the same" herein implies a range of |hc−ho|≤several cm. Further, assuming that the length La of the hollow portion 40 is 100, the length Lf of the third negative electrode 54c and the length Lg of the third positive electrode 56c lie within a range of 5 to 10.

Next, operations of the third particle counter 10C will be described with reference to FIGS. 3 and 4.

Figure 3:
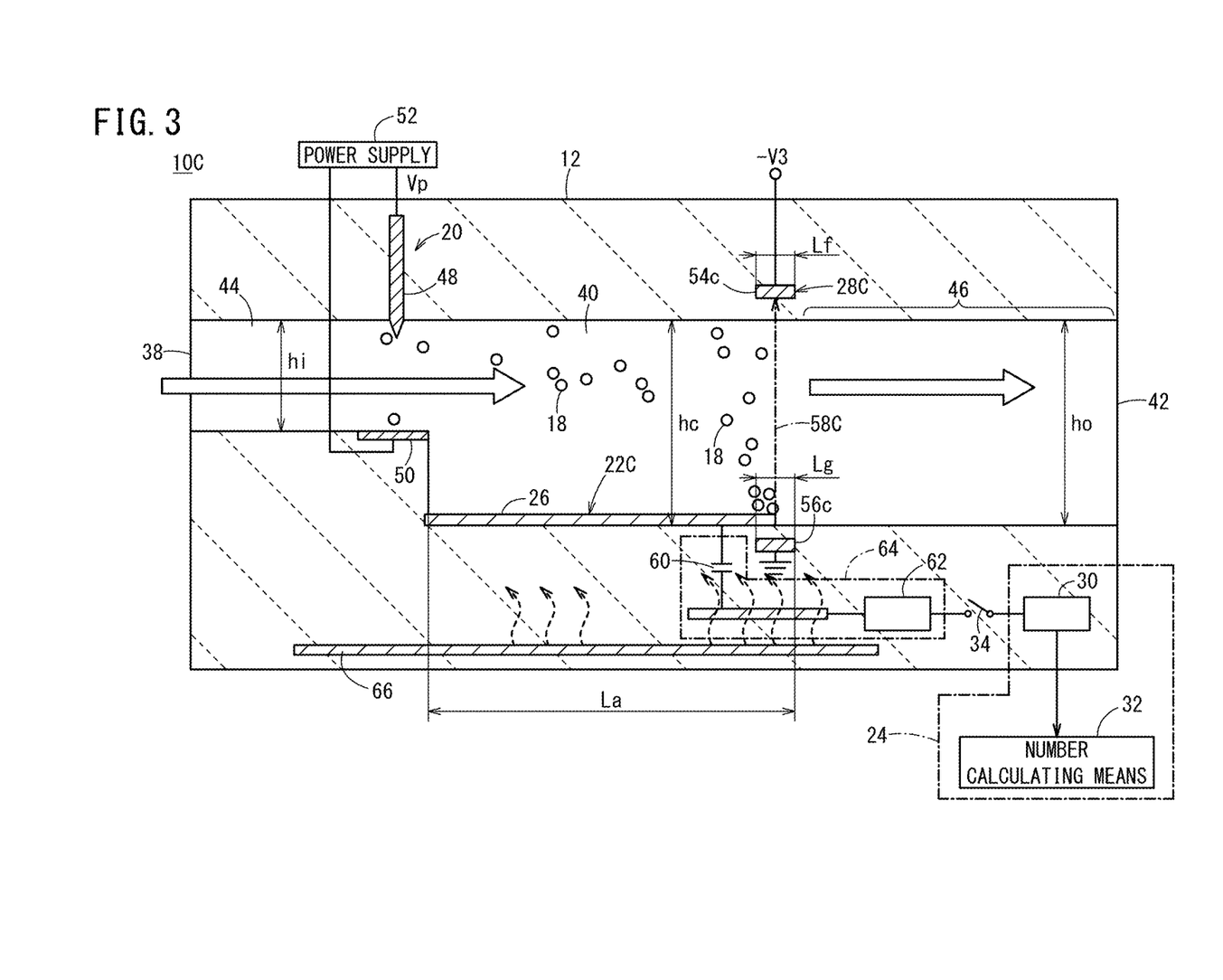
FIG. 3 is a diagram showing the structure of a particle counter according to a third embodiment of the present invention (in which no measurement target gas containing particles is supplied)

First, as shown in FIG. 3, the third particle counter 10C is operated in an environment in which almost no particles 16 are present (e.g., in a clean room). More specifically, $-V3$ is applied to the third negative electrode 54c. Thus, a third electric field 58C, which is oriented from the third positive electrode 56c toward the third negative electrode 54c, is generated. The intensity of the third electric field 58C is smaller than the intensity of the first electric field 58A. At this time, electric charges 18 generated by corona discharge in the electric charge adding means 20 are drawn toward the third positive electrode 56c by the generated third electric field 58C, and are collected at the measurement electrode 26, which is provided at an intermediate position on the way to the third positive electrode 56c. In addition, by turning on the switch 34, an electric current I based on the electric charges 18 collected at the measurement electrode 26 is signaled to the current measuring unit 30 as a transient response through the serial circuit 64.

The number calculating means 32 integrates (accumulates) electric current values from the current measuring unit 30 at fixed time intervals (e.g., 5 to 15 seconds), over a period of time in which an on-operation of the switch 34 is performed (ON period), in order to determine an integrated value (accumulated electric charge quantity) of electric current values at the fixed time intervals. The accumulated electric charge quantity determined at the fixed time intervals is divided by the charge quantity of one piece of electric charge. In this manner, it is possible to determine the number of electric charges that become adhered to the measurement electrode 26 at the fixed time intervals. The changes in the number of electric charges within each fixed time period are plotted. The number of electric charges at a stage in which the number of electric charges becomes maximum is defined virtually as the number of electric charges when no particles are present.

Figure 4:
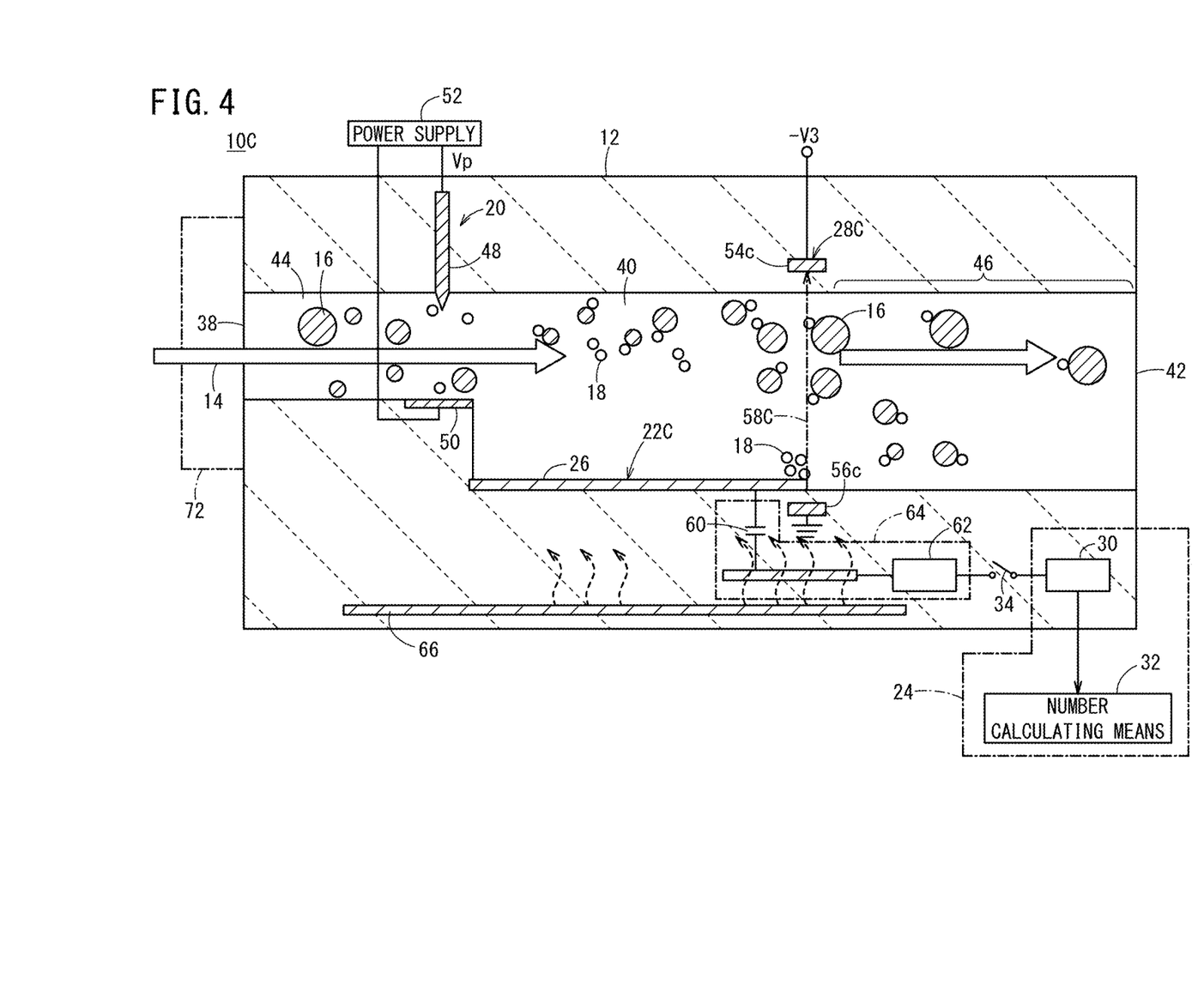
FIG. 4 is a diagram showing the structure of a particle counter according to a third embodiment of the present invention (in which a measurement target gas containing particles is supplied).

Thereafter, as shown in FIG. 4, a measurement target gas 14 containing the particles 16 is supplied into the casing 12 of the third particle counter 10C.

Some of the electric charges 18 generated as a result of corona discharge by the electric charge adding means 20 are added to the particles 16 contained within the measurement target gas 14, and move together with the particles 16 toward the gas outlet 46 through the hollow portion 40. The particles 16 that have entered into the hollow portion 40 are drawn toward the third positive electrode 56c by the generated third electric field 58C. However, since the third positive electrode 56c is provided in the vicinity of the gas outlet 46, and the length Lg (see FIG. 3) of the third positive electrode 56c is short, i.e., within a range of $\frac{1}{20}$ to $\frac{1}{10}$ of the length La of the hollow portion 40, the change in the flow channel (path) of the particles 16 due to the third electric field 58C starts immediately before arrival thereof at the gas outlet 46. Further, although the third electric field 58C operates to significantly change the path of the electric charges 18, since the intensity of the third electric field 58C is smaller than that of the first electric field 58A, no significant change occurs in the path of the particles 16. As a result, the particles 16 are not collected at the measurement electrode 26, and move directly toward the gas outlet 46. As described above, since the electric charges 18 that are added to the particles 16 are discharged to the outside together with the particles 16, the electric charges 18 are not collected at the measurement electrode 26. That is, in the case that the measurement target gas 14 is supplied, it can be understood that the number of electric charges 18 collected at the measurement electrode 26 is smaller, by an amount corresponding to the number of the particles 16, than a case in which no measurement target gas 14 is supplied.

Thus, in a stage at which the measurement target gas 14 is supplied, by subtracting the number of electric charges 18 within the fixed time period from the maximum number of the electric charges 18 within the fixed time period, it is possible to determine the number of particles 16 within the fixed time period.

It is a matter of course that an alarm may be issued when the number of particles 16 within the fixed time period reaches a predetermined value or more, e.g., a predetermined regulation value or more. In this case, in the stage at which the measurement target gas 14 is supplied, instead of subtracting the number of electric charges 18 from the maximum number of the electric charges 18, an alarm may be issued in the case that the number of electric charges 18 within the fixed time period in the stage at which the measurement target gas 14 is supplied is decreased below the predetermined threshold value. As such a threshold value, for example, a value obtained by subtracting the regulation value from the above maximum number of electric charges may be adopted.

The third particle counter 10C may also be used for measuring the number of particles 16 having a predetermined particle size or less (e.g., less than 2.5 μm).

In this case, in order to prevent entry of particles 16 having a predetermined partition size or more into the casing 12, for example, it is preferable to provide a member 72 for removing particles 16 having a predetermined particle size or more at the gas supply port 38 (shown by the two-dot-dashed line in FIG. 4). As such a member 72, for example, a HEPA filter (High Efficiency Particulate Air Filter) or the like may be used. In this manner, it becomes possible to count the number of particles 16 having a particle size of 2.5 μm or less at fixed time intervals (e.g., 5 to 15 seconds). Further, it becomes possible to easily realize an application in which an alarm is issued when the number of particles 16 having a particle size of 2.5 μm or less reaches the regulation value or more, or reaches $1/10$, $1/5$, etc., of the regulation value.

It is a matter of course that the particle counter and the method of counting the number of particles according to the present invention is not limited to the embodiments described above, and various structures can be adopted without deviating from the gist of the present invention.

What is claimed is:

1. A particle counter comprising:
   a casing made of ceramic;
   an electric charge adder configured to add electric charges to particles in a measurement target gas supplied into the casing;
   an electric charge collector configured to collect the electric charges added to the particles; and
   a number measuring unit configured to measure a number of the particles based on a quantity of the collected electric charges; wherein
   the electric charge adder includes a needle electrode oriented toward an inlet of the particles in the casing, and a counter electrode provided in opposition to a front end of the needle electrode; and
   a corona discharge is generated between the needle electrode and the counter electrode by a potential difference between the needle electrode and the counter electrode.

2. The particle counter according to claim 1, further comprising a heater configured to heat a portion where the electric charges are collected.

3. The particle counter according to claim 1, further comprising a switch configured to electrically connect the electric charge collector and the number measuring unit at fixed time intervals,
   wherein the number measuring unit measures an electric current based on the quantity of the collected electric charges.

4. The particle counter according to claim 3, wherein a serial circuit including a capacitor and a resistor is connected to the electric charge collector; and
   when the electric charge collector and the number measuring unit are electrically connected by the switch, generation of electric current based on the electric charges collected by the electric charge collector is signaled to the number measuring unit as a transient response through the serial circuit.

5. The particle counter according to claim 1, wherein the electric charge collector includes a measurement electrode provided in the casing, and at least one electric field generator configured to generate an electric field in the casing; and
   the electric charges added to the particles are collected at the measurement electrode by the electric field.

6. The particle counter according to claim 5, wherein the electric field generator of the electric charge collector includes a negative electrode provided in the casing at a position deeper than an inlet of the particles, and a positive electrode provided in opposition to the negative electrode; and
   the measurement electrode of the electric charge collector is provided between the negative electrode and the positive electrode, and is arranged in vicinity of the positive electrode.

7. The particle counter according to claim 6, wherein the positive electrode and the negative electrode are embedded in the casing.

8. The particle counter according to claim 1, further comprising at least one electric field generator, together with a second electric charge collector configured to collect electric charges that have not been added to the particles.

9. A method of counting a number of particles, comprising the steps of:
   adding electric charges to particles in a measurement target gas supplied into a casing made of ceramic;
   collecting the electric charges added to the particles; and
   measuring the number of the particles based on a quantity of the collected electric charges; wherein
   adding the electric charges includes orienting a needle electrode toward an inlet of the particles in the casing, and providing a counter electrode in opposition to a front end of the needle electrode; and
   generating a corona discharge between the needle electrode and the counter electrode by a potential difference between the needle electrode and the counter electrode.

* * * * *